United States Patent
Delfort et al.

(12)

(10) Patent No.: US 6,339,163 B1
(45) Date of Patent: Jan. 15, 2002

(54) TETRAHYDROFURAN DERIVATIVES THAT CAN BE USED AS DETERGENT COMPOSITIONS FOR GASOLINE-TYPE FUELS

(75) Inventors: Bruno Delfort, Paris; Stéphane Joly, Bougival; Thierry Lacôme, Garches; Patrick Gateau, Maurepas; Fabrice Paille, Limay, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/637,835

(22) Filed: Aug. 11, 2000

(30) Foreign Application Priority Data

Aug. 12, 1999 (FR) .............................................. 99 10505

(51) Int. Cl.[7] .......................... C07D 307/06; C10L 1/16; C10L 1/18
(52) U.S. Cl. ......................... 549/502; 44/329; 510/108
(58) Field of Search .............................. 549/502; 44/329

(56) References Cited

U.S. PATENT DOCUMENTS

| 3,382,055 A | 5/1968 | Jacobson et al. ............... 44/62 |
| 4,481,123 A | 11/1984 | Hentschel et al. |
| 5,741,946 A | 4/1998 | Wei ............................. 568/617 |

FOREIGN PATENT DOCUMENTS

| DE | 3210283 A1 | 9/1983 |
| DE | 3244077 A1 | 5/1984 |
| EP | 0 665 206 A1 | 8/1995 |
| JP | 03062898 | * 7/1989 |
| WO | WO 94/14925 | 7/1994 |
| WO | WO 95/17484 | 6/1995 |
| WO | WO 98/44022 | 10/1998 |

OTHER PUBLICATIONS

Baark, et. al, 1990, J. Pharm. Pharmacol., 42(12), 837–41.*

* cited by examiner

*Primary Examiner*—Floyd D. Higel
*Assistant Examiner*—Andrea M. D'Souza
(74) *Attorney, Agent, or Firm*—Millen, White, Zelano & Branigan, P.C.

(57) ABSTRACT

Compositions that comprise at least one compound that corresponds to general formula (I):

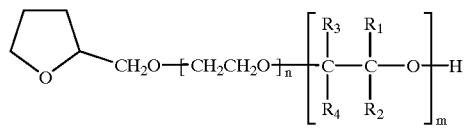

in which n is a number from 0 to 20; $R_1$, $R_2$, $R_3$ and $R_4$ each represent a hydrogen atom or a hydrocarbon radical, for example alkyl, with 1 to 30 carbon atoms, whereby at least one of $R_1$, $R_2$, $R_3$, and $R_4$ is a hydrocarbon radical; and m is a number from 1 to 30, can be prepared by a process that comprises the reaction of a hydroxymethylated derivative of tetrahydrofuran with ethylene oxide, then with one or more other epoxidized compounds. These compositions can be used as detergent additives for gasoline-type fuels.

10 Claims, No Drawings

TETRAHYDROFURAN DERIVATIVES THAT CAN BE USED AS DETERGENT COMPOSITIONS FOR GASOLINE-TYPE FUELS

The invention relates to new compounds that can be used by themselves or in mixtures as detergent additive compositions for fuels.

It is known that automobile engines have a tendency to form deposits on the surface of the engine elements, in particular on the carburetor orifices, the bodies of butterfly valves, fuel injectors, cylinder orifices and intake valves, because of oxidation and polymerization of various hydrocarbon-containing components of the fuel. These deposits, even when they are present only in small amounts, are often responsible for significant driving problems, such as the engine timing and poor acceleration. In addition, deposits in the engine can significantly increase the consumption of fuel and the production of pollutants. This is why the development of effective detergent additives for regulating these deposits assumes a considerable importance and was already the object of much research.

A new family of compounds that exhibit good effectiveness as additives that are intended to reduce the deposits in the injectors and in the intake valves has now been discovered.

The compounds of the invention can be defined by the following general formula (I):

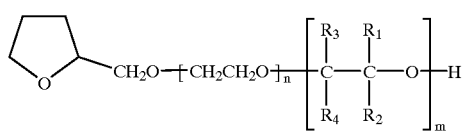

in which n is a number from 0 to 20, preferably 0 to 10; R1, R2, R3, and R4 each represent a hydrogen atom or a hydrocarbon radical, for example alkyl, with 1 to 30 carbon atoms, whereby at least one of R1, R2, R3, and R4 is a hydrocarbon radical; and whereby the concatenations:

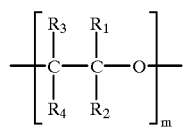

can consist of patterns:

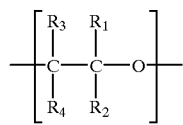

that differ from one another by the nature of R1, R2, R3 and/or R4; and m is a number from 1 to 30.

The compounds of the invention generally come in the form of mixtures of compounds that differ from one another by the value of n, and/or by the nature of at least one of radicals R1 to R4. It is then a matter of compositions.

The synthesis of the compounds or compositions defined above can be carried out as described below. It generally comprises the reaction of a hydroxymethylated derivative of tetrahydrofuran with ethylene oxide, then with one or more other epoxidized compounds.

The hydroxymethylated derivative of tetrahydrofuran, such as, for example, 2-(hydroxymethyl) tetrahydrofuran, is mixed with, for example, sodium hydride. After having purged, under stirring, the reactor of the released hydrogen, the ethylene oxide is optionally introduced in an amount that is calculated to obtain the desired value of n, and the medium is brought to a temperature of 60 to 130° C., then epoxide or a mixture of epoxides of general formula

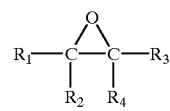

in which R1, R2, R3 and R4 are defined as above, is added at an amount that is calculated to obtain the desired value of m, and the medium is brought to a temperature of 80 to 180° C., and the reaction mixture is kept at this temperature until the end of the consumption of the epoxide or epoxides.

After returning to ambient temperature, the medium is diluted with an organic solvent, for example a hydrocarbon solvent, such as heptane, it is washed with water one or more times, then, after evaporation under reduced pressure of the organic phase, the product that corresponds to general formula (I) is obtained:

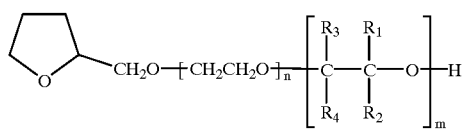

The compositions of the invention can be used as detergent additives in the gasoline-type fuels. In this application, they can be added to the fuels at concentrations of, for example, 20 to 5000 mg per liter. They can also be used mixed with any other detergent compound.

The following examples illustrate the invention without limiting its scope.

EXAMPLE 1

In a reactor that makes it possible to operate under pressure, equipped with a stirring system, a system for introducing reagents, a system for measuring temperature and pressure, 10.2 g (0.1 mol) of 2-tetrahydrofuranyl-hydroxymethane and 0.12 g of sodium hydride are introduced. After having purged, under stirring, the reactor of the released hydrogen, 17.6 g (0.4 mol) of ethylene oxide is introduced, and then the medium is brought to the temperature of 110° C., and it is kept at this temperature until the drop in pressure indicates the end of the consumption of ethylene oxide. After returning to ambient temperature, 100 g (1.39 mol) of 1,2-epoxybutane is introduced, then the medium is gradually brought to the temperature of 145° C., and it is kept at this temperature until the drop in pressure indicates the end of the consumption of 1,2-epoxybutane. After returning to ambient temperature, the medium is diluted with heptane, washed with 2×50 g of water, then, after evaporation under reduced pressure of the organic phase, 123 g of a clear pale yellow liquid is obtained that is soluble in gasoline and whose structure corresponds to the general formula:

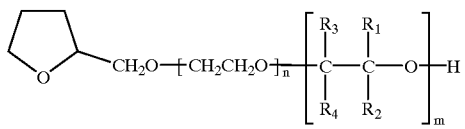

in which

R1=R3=R4=H; R2=—CH2—CH3;

$n_{mean}=4$; and $m_{mean}=14$.

EXAMPLE 2

In a reactor that makes it possible to operate under pressure, equipped with a stirring system, a system for introducing reagents, and a system for measuring temperature and pressure, 10.2 g (0.1 mol) of 2-tetrahydrofuranyl-hydroxymethane and 0.12 g of sodium hydride are introduced. After having purged, under stirring, the reactor of the released hydrogen, 100 g (1.39 mol) of 1,2-epoxybutane is introduced. The medium is gradually brought to the temperature of 145° C., and it is kept at this temperature until the drop in pressure indicates the end of consumption of 1,2-epoxybutane. After returning to ambient temperature, the medium is diluted with heptane, washed with 2×50 g of water, then, after evaporation under reduced pressure of the organic phase, 107 g of a clear pale yellow liquid is obtained that is soluble in gasoline and whose structure corresponds to the general formula:

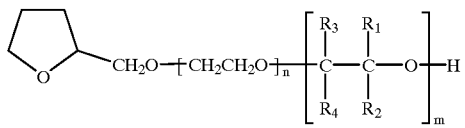

in which

R1=R3=R4=H; R2=—CH2—CH3;

$n_{mean}=0$; and $m_{mean}=14$.

EXAMPLE 3

In a reactor that makes it possible to operate under pressure, equipped with a stirring system, a system for introducing reagents, a system for measuring temperature and pressure, 10.2 g (0.1 mol) of 2-tetrahydrofuranyl-hydroxymethane and 0.2 g of sodium hydride are introduced. After having purged, under stirring, the reactor of the released hydrogen, 35.2 g (0.8 mol) of ethylene oxide is introduced, and then the medium is brought to the temperature of 110° C., and it is kept at this temperature until the drop in pressure indicates the end of the consumption of ethylene oxide. After returning to ambient temperature, 130 g (1.81 mol) of 1,2-epoxybutane is introduced, then the medium is gradually brought to the temperature of 145° C., and it is kept at this temperature until the drop in pressure indicates the end of the consumption of 1,2-epoxybutane. After returning to ambient temperature, the medium is diluted with heptane, washed with 2×50 g of water, then, after evaporation under reduced pressure of the organic phase, 170 g of a clear pale yellow liquid is obtained that is soluble in gasoline and whose structure corresponds to the general formula:

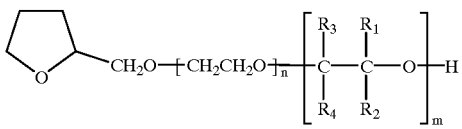

in which

R1=R3=R4=H; R=—CH2—CH3;

$n_{mean}=8$; and $m_{mean}=14$.

EXAMPLE 4

In a reactor that makes it possible to operate under pressure, equipped with a stirring system, a system for introducing reagents, a system for measuring temperature and pressure, 10.2 g (0.1 mol) of 2-tetrahydrofuranyl-hydroxymethane and 0.12 g of sodium hydride are introduced. After having purged, under stirring, the reactor of the released hydrogen, 17.6 g (0.4 mol) of ethylene oxide is introduced, and then the medium is brought to the temperature of 110° C., and it is kept at this temperature until the drop in pressure indicates the end of the consumption of ethylene oxide. After returning to ambient temperature, 129.6 g (1.8 mol) of 1,2-epoxybutane is introduced, then the medium is gradually brought to the temperature of 145° C., and it is kept at this temperature until the drop in pressure indicates the end of the consumption of 1,2-epoxybutane. After returning to ambient temperature, the medium is diluted with heptane, washed with 2×50 g of water, then, after evaporation under reduced pressure of the organic phase, 140 g of a clear pale yellow liquid is obtained that is soluble in gasoline and whose structure corresponds to the general formula:

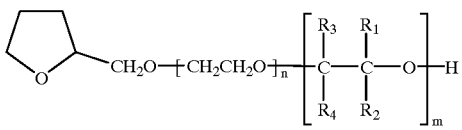

in which

R1=R3=R4=H; R=—CH2—CH3;

$n_{mean}=4$; and $m_{mean}=18$.

EXAMPLE 5

The products that are prepared in the preceding examples are evaluated as additives for their detergent properties at a concentration of 400 mg/liter in an unleaded gasoline with a "research" octane number of 96.8 and whose characteristics are as follows:

| | |
|---|---|
| Density at 15° C. | 753.9 kg/m$^3$ |
| Reid vapor pressure | 60.2 kPa |
| Lead content | <2 mg/l |
| Distillation | |
| Starting point | 33.0° C. |
| 5% | 45.9° C. |
| 10% | 51.2° C. |
| 20% | 61.1° C. |
| 30% | 73.1° C. |
| 40% | 88.3° C. |
| 50% | 104.2° C. |

-continued

| | |
|---|---|
| 60% | 116.0° C. |
| 70% | 125.6° C. |
| 80% | 138.5° C. |
| 90% | 155.6° C. |
| 95% | 169.8° C. |
| End point | 189.0° C. |

The evaluation is carried out with a test on a Mercedes M102E engine according to the CEC-F-05-A-93 method. The duration of this test is 60 hours. This method makes it possible to evaluate the amount of deposits that are formed on the intake valves of the engine.

The results that appear in the following table show the effect of the products of the invention for reducing the deposits on the intake valves.

TABLE

| Additive | Content (mg/l) | Deposited Material on the Intake Valves (mg) | | | | |
|---|---|---|---|---|---|---|
| | | Valve 1 | Valve 2 | Valve 3 | Valve 4 | Mean |
| None | 0 | 241 | 275 | 272 | 312 | 275 |
| Product of Example 1 | 400 | 113 | 100 | 108 | 69 | 97.5 |
| Product of Example 4 | 400 | 22 | 21 | 29 | 35 | 26.7 |

What is claimed is:

1. A method of using a compound as a detergent additive in a gasoline which comprises adding a compound of formula I to a gasoline

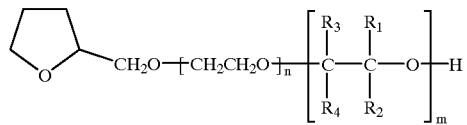

in which n is a number from 0 to 20, $R_1$, $R_2$, $R_3$, and $R_4$ each represent a hydrogen atom or a hydrocarbon radical with 1 to 30 carbon atoms, whereby at least one of $R_1$, $R_2$, $R_3$ and $R_4$ is a hydrocarbon radical and m is a number from 1 to 30.

2. A method of using a composition as a detergent additive in a gasoline which comprises adding a composition to a gasoline said composition comprising a mixture of compounds of formula I which differ from one another by a) the value of n, b) the nature of at least one of the radicals, $R_1$, $R_2$, $R_3$ or $R_4$, or c) both a) and b)

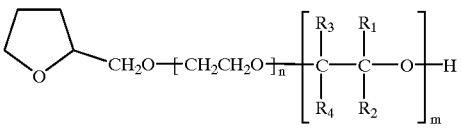

in which n is a number from 0 to 20, $R_1$, $R_2$, $R_3$, and $R_4$ each represent a hydrogen atom or a hydrocarbon radical with 1 to 30 carbon atoms, whereby at least one of $R_1$, $R_2$, $R_3$ and $R_4$ is a hydrocarbon radical and m is a number from 1 to 30.

3. A method as in claim 1, wherein said compound is used in a mixture with another detergent compound.

4. A method as in claim 2, wherein said composition is used in a mixture with another detergent compound.

5. A method as in claim 1, wherein the amount of compound of formula I added to a gasoline provides a concentration of compound of formula I that falls within the range of 20–5000 mg/liter.

6. A method as in claim 2, wherein the amount of said composition added to a gasoline provides a concentration of said composition that falls within the range of 20–5000 mg/liter.

7. A gasoline composition which comprises a compound of formula I

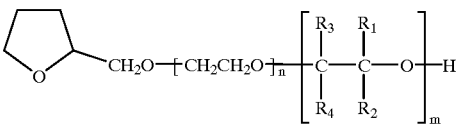

in which n is a number from 0 to 20, $R_1$, $R_2$, $R_3$ and $R_4$ each represent a hydrogen atom or a hydrocarbon radical with 1 to 30 carbon atoms, whereby at least one of $R_1$, $R_2$, $R_3$ and $R_4$ is a hydrocarbon radical and m is a number from 1 to 30.

8. A gasoline composition which comprises a mixture of compounds of formula I that differ from one another by a) the value of n, b) the nature of at least one of the radicals $R_1$, $R_2$, $R_3$, and $R_4$, c) or both a) and b).

9. A gasoline composition as in claim 7, wherein the concentration of the compound of formula I falls within the range of 20–5000 mg/liter.

10. A gasoline composition as in claim 8, wherein the concentration of the mixture of compounds of formula I falls within the range of 20–5000 mg/liter.

* * * * *